US012514728B1

(12) United States Patent
Ringgold

(10) Patent No.: US 12,514,728 B1
(45) Date of Patent: Jan. 6, 2026

(54) ANKLE ORTHOSIS

(71) Applicant: Justin Ringgold, Clovis, NM (US)

(72) Inventor: Justin Ringgold, Clovis, NM (US)

( * ) Notice: Subject to any disclaimer, the term of this patent is extended or adjusted under 35 U.S.C. 154(b) by 249 days.

(21) Appl. No.: 18/216,484

(22) Filed: Jun. 29, 2023

Related U.S. Application Data

(60) Provisional application No. 63/359,624, filed on Jul. 8, 2022.

(51) Int. Cl.
*A61F 5/01* (2006.01)

(52) U.S. Cl.
CPC ........... *A61F 5/0111* (2013.01); *A61F 5/0113* (2013.01)

(58) Field of Classification Search
CPC ...... A61F 5/011; A61F 5/0113; A61F 5/0127; A43B 7/18; A43B 7/20
See application file for complete search history.

(56) References Cited

U.S. PATENT DOCUMENTS

| | | | | |
|---|---|---|---|---|
| 2,584,010 A * | 1/1952 | Goffredo | A61F 5/0113 | 602/28 |
| 4,817,589 A * | 4/1989 | Wertz | A61F 5/0111 | 602/28 |
| 4,928,405 A * | 5/1990 | Spademan | A43C 11/16 | 36/50.1 |
| 7,094,213 B1 * | 8/2006 | Cook | A61F 13/065 | 602/65 |
| 7,458,950 B1 * | 12/2008 | Ivany | A43B 7/14 | 602/5 |
| 7,674,212 B2 * | 3/2010 | Kruijsen | A61F 5/0113 | 482/907 |
| 2012/0029401 A1 * | 2/2012 | Caldwell | A61F 5/0113 | 602/16 |
| 2014/0276318 A1 * | 9/2014 | Faux | A61F 5/0109 | 602/28 |
| 2015/0150705 A1 * | 6/2015 | Capra | A61F 5/0123 | 602/6 |
| 2015/0374527 A1 * | 12/2015 | Wenger | A43C 5/00 | 602/28 |
| 2016/0067075 A1 * | 3/2016 | Malinowski | A61F 5/0113 | 602/28 |
| 2020/0352780 A1 * | 11/2020 | Katz | A61F 7/02 | |

* cited by examiner

*Primary Examiner* — Keri J Nelson
(74) *Attorney, Agent, or Firm* — MALLOY & MALLOY, PL

(57) ABSTRACT

The present invention relates to an improved ankle orthosis designed to promote proper ankle movement and potentially prevent ankle injuries. The orthosis attaches to the distal shin above the lateral and medial malleolus through a conforming back strap with a rigid adjustable strap that connects to a resistive strap. This assembly is anchored to the distal dorsal aspect of the wearer's conventional shoe. The orthosis provides dynamic, adaptable support without restricting motion. It enhances balance performance by increasing sensory input from compression of the distal shin and facilitates proper ankle range of motion. Additionally, the orthosis may assist in preventing ankle sprains by aiding in the transition from plantarflexion to dorsiflexion. The device is simple to use and includes a customizable spandex cover for aesthetic appeal and added protection.

19 Claims, 8 Drawing Sheets

ANKLE ORTHOSIS

FIELD OF THE INVENTION

The present invention relates generally to orthosis, and more particularly, to an ankle orthosis which promotes proper ankle movement.

BACKGROUND OF THE INVENTION

The human ankle is an intricate structure consisting of three main bones: the tibia, fibula, and talus, connected through various ligaments and tendons. This joint is particularly significant as it bears the entire weight of the body and provides stability during movement, be it walking, running, or any other physical activity. Despite its robust construction, the ankle is susceptible to injury due to its heavy workload and the complex mechanics it employs. One common injury is a sprain, which occurs when the ligaments that support the ankle stretch beyond their limits and tear. Other complications may include strains, fractures, and chronic conditions like arthritis.

In recent years, advancements in orthopedic medicine have led to the development of numerous interventions and therapeutic devices designed to treat and prevent ankle injuries. These interventions often aim to provide stability, reduce pain, aid recovery, and prevent future injuries. Ankle orthoses are one such intervention. These devices, which are worn around the ankle, can support the joint, aid in correct biomechanical function, and in some instances, provide a degree of immobilization to allow for healing.

Traditional ankle orthoses generally fall into two categories: functional and prophylactic. Functional orthoses are used after an injury has occurred, aiding the healing process by providing support to the affected area, reducing swelling, and controlling the range of motion. Prophylactic orthoses are used to prevent injury, typically in individuals at a higher risk due to their involvement in physically demanding activities, or those with a history of previous ankle injuries.

While these traditional ankle orthoses have made significant contributions to ankle rehabilitation and prevention, they do have limitations. Many of these devices restrict the user's range of motion, leading to discomfort during extended periods of use. They may also impede the natural movement of the ankle, thereby inhibiting the joint's healing and retraining process. Some orthoses lack adaptability, failing to cater to a variety of ankle conditions and user needs. Moreover, many conventional designs do not offer significant sensory input, which is crucial for balance and proprioception—the sense of the relative position of one's own parts of the body and the strength of effort employed in movement.

Existing orthoses often disregard arthrokinematics, the study of the motion of joints in the body, and osteokinematics, the relationship between the movement of bones around a joint axis. Both arthrokinematics and osteokinematics play an integral role in understanding the complexities of joint motion. For instance, the natural roll and glide of the ankle joint, which is the fundamental motion allowing for efficient movement and joint health, is often overlooked in the design of traditional ankle orthoses.

Another limitation of conventional orthoses is the over-reliance on non-dynamic, rigid structures to provide support. While these structures may offer stability, they often limit natural movement and could lead to muscle atrophy due to decreased use of the joint. Moreover, these rigid orthoses might not offer much assistance in the transition from plantarflexion to dorsiflexion, a common movement that involves shifting from pointing the toes (as in jumping) to having the toes neutral or dorsiflexed (as in landing). This transition is crucial in many physical activities, and its improper execution can contribute to ankle sprains.

Additionally, current orthoses usually offer a one-size-fits-all solution, failing to consider that each individual's ankle characteristics can vary greatly. This approach can compromise the fit and effectiveness of the device, leading to discomfort and sub-optimal support. Furthermore, some orthoses may not cater to users with different types of footwear, limiting their versatility and applicability.

Lastly, aesthetics and comfort are often overlooked in the design of traditional orthoses. This lack of consideration can lead to decreased user compliance, especially for individuals who are required to wear these devices for extended periods.

With these limitations in mind, there is a growing need for an ankle orthosis that is adaptable, dynamic, comfortable, and promotes natural joint movement. An improved orthosis should consider arthrokinematics and osteokinematics, facilitating the natural roll and glide of the ankle joint. Such a device should be adjustable, accommodating a variety of user needs, and should work seamlessly with different types of footwear. A novel ankle orthosis should not only support the ankle but also promote improved balance performance, aid in the transition from plantarflexion to dorsiflexion, and offer enhanced sensory input. Lastly, such a device should be simple to use and aesthetically pleasing, encouraging user compliance and satisfaction.

This need in the orthopedic field has led to the invention disclosed herein-a multifaceted ankle orthosis designed to address the limitations of traditional devices while introducing innovative features for improved ankle support and rehabilitation.

SUMMARY OF THE INVENTION

The present invention is directed to an orthosis for an ankle which can be worn by a user to help improve the way the Talocrural joint (TCJ) glides/slides/moves by assisting the natural roll and glide of the joint. The presently disclosed ankle orthosis may further help with balance, improve range of motion (ROM) and prevent ankle sprains.

The presently disclosed ankle orthosis may be worn while walking, hiking, running, and/or jumping to prevent ankle pain or injury such as sprains in sports or activities that require mild to heavy ankle use. The presently disclosed ankle orthosis may further help keep pressure on the distal shin parallel to the surface of the concave TCJ in neutral alignment. The presently disclosed ankle orthosis may protect user's ankle from overly extended dorsiflexions and plantarflexions.

In a first implementation of the invention, an ankle orthosis comprises a strap and anchors coupled with the ends of the strap. The strap is of sufficient length to partially wrap around wearer's leg, attach with user's shoe, and retain a support member between the user's shoe and the strap.

In a second aspect, the anchors are coupled with the ends of the strap are configured to couple with user's shoe adjacent to user's toes.

In another aspect, the anchors are coupled with eyelets of the user's shoe.

In another aspect, the anchors are coupled with shoelace of the user's shoe.

In another aspect, the strap comprises a pad.

In another aspect, the support member is adjustable.

In another aspect, the strap is configured to apply forward force to user's leg.

In another aspect, the strap is configured to urge user's leg forward.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

DETAILED DESCRIPTION

Figure 1:
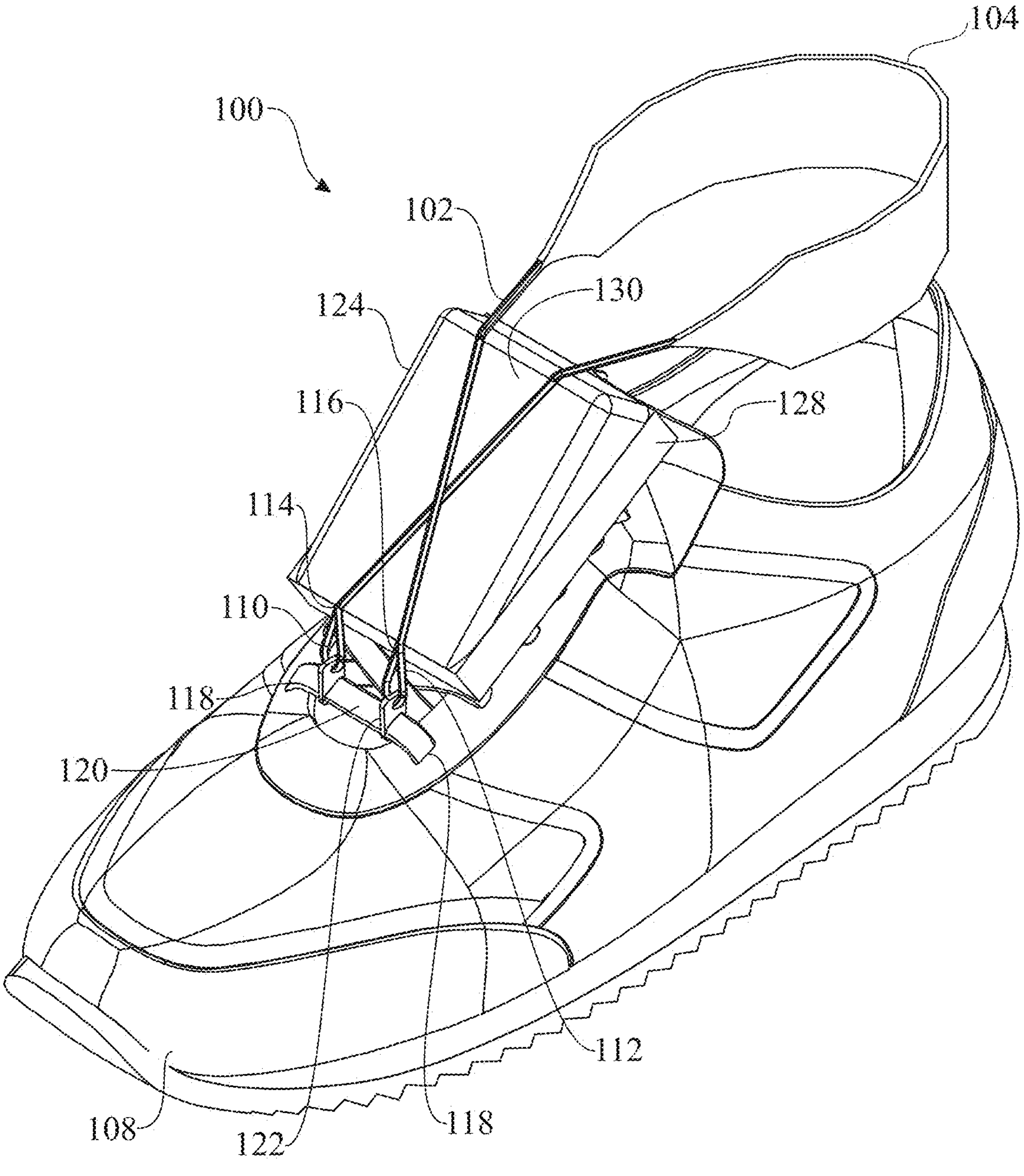
FIG. 1 presents a front isometric view of an ankle orthosis in accordance with some of the embodiments of the present invention.
Figure 2:
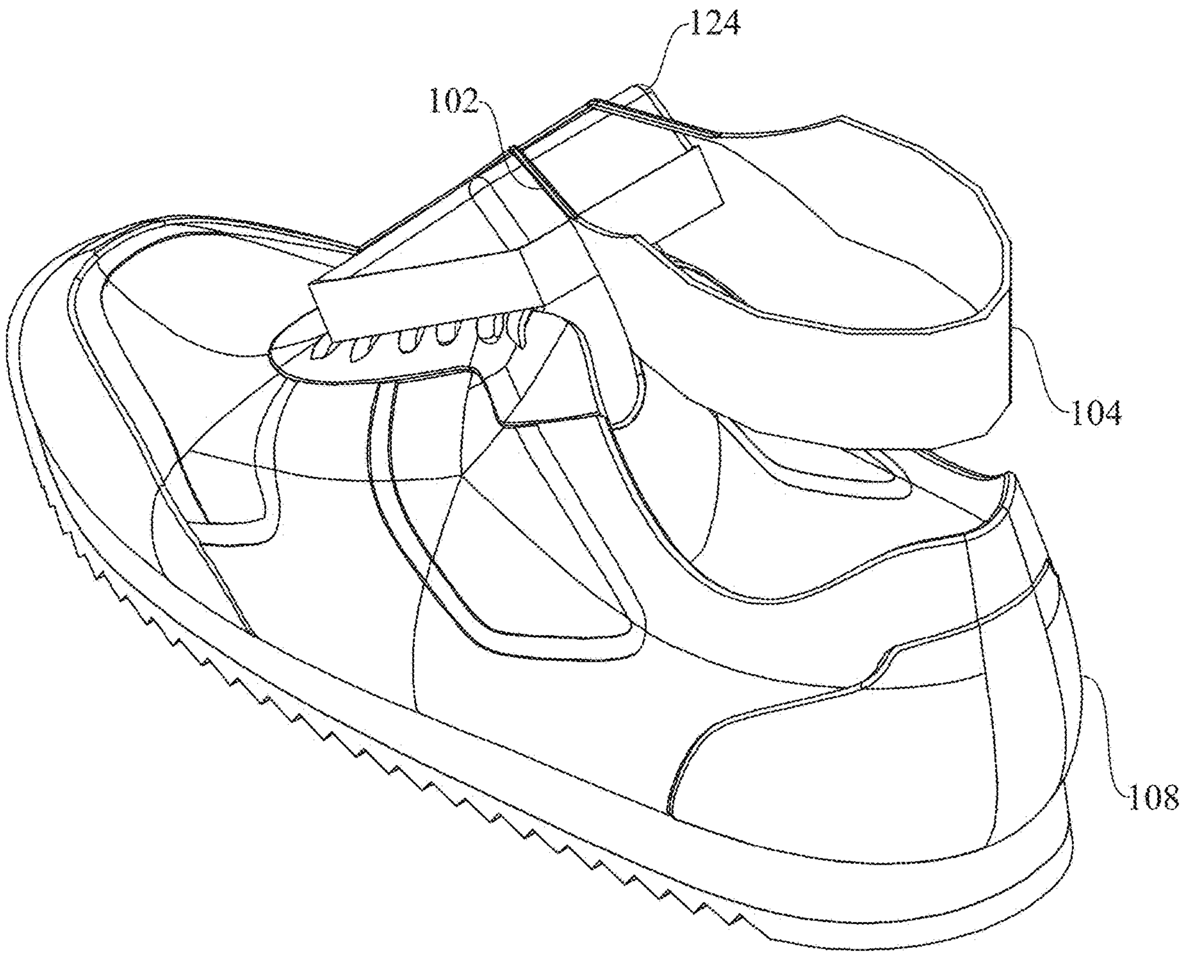
FIG. 2 presents a rear isometric view of the ankle orthosis illustrated in FIG. 1.
Figure 3:
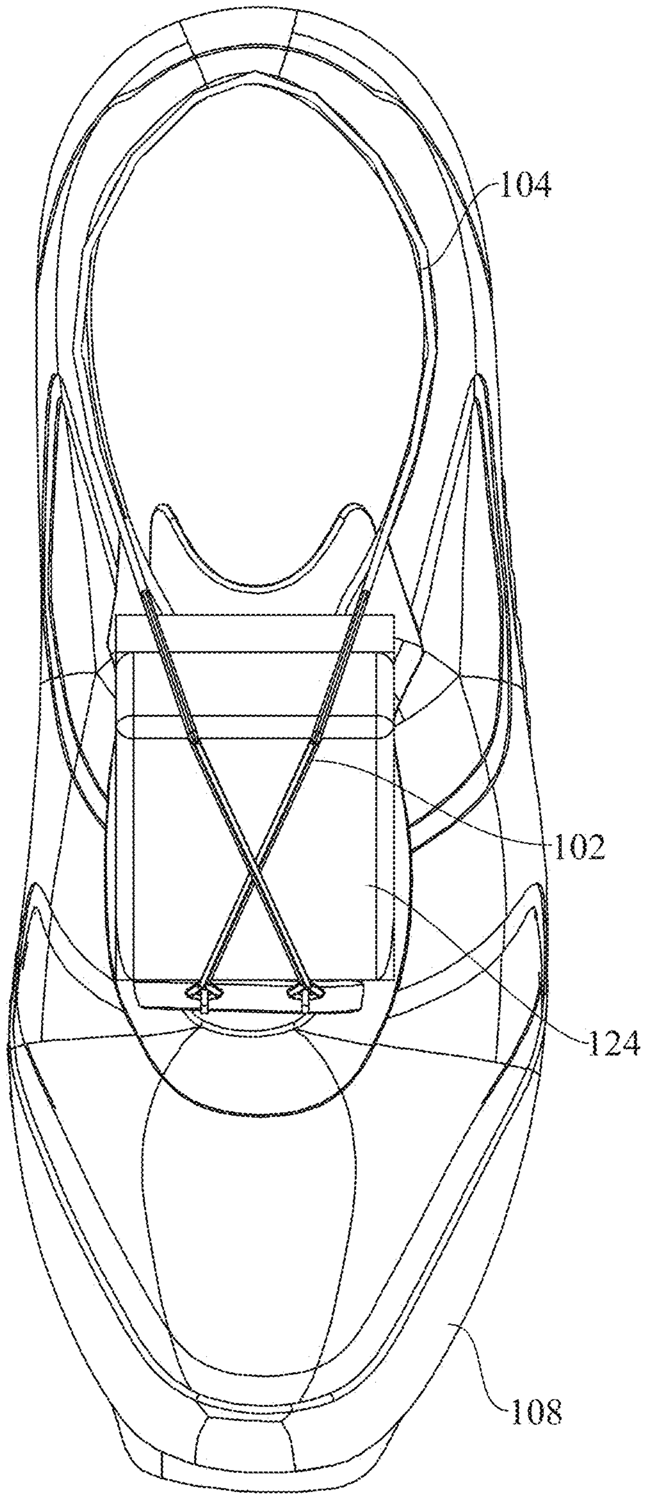
FIG. 3 presents a top view of the ankle orthosis illustrated in FIG. 1.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

In accordance with certain embodiments, an ankle orthosis as described herein can be affixed at the lower shin above the lateral and medial malleolus utilizing a back strap that incorporates a rigid adjustable strap. This strap connects to a resilient, spring-like strap via rigid connectors, anchoring at the lower dorsal aspect of the user's standard footwear.

In certain embodiments, a custom spandex cover might be employed to encapsulate and shield the aforementioned ankle orthosis.

The described ankle orthosis is convenient, adaptable, and dynamic, enabling unimpeded motion. It fosters better balance performance owing to heightened sensory input from lower shin compression, facilitates correct ankle range of motion through assistance with arthrokinematics and osteokinematics, and potentially reduces ankle sprains by aiding the transition from plantarflexion to dorsiflexion, thus averting joint dysfunction.

In certain embodiments, this multifaceted orthosis is engineered to enhance the performance of the Talocural joint (TCJ), facilitating its natural rolling and gliding movements as outlined by basic arthrokinematics and osteokinematics. The orthosis further promotes proper joint function, addressing TCJ dysfunction that can result from trauma, surgery, or overuse. Additionally, it supports functional ankle movement that can treat or prevent ankle ailments.

Certain embodiments feature a back strap conforming to the lower shin above the lateral and medial malleolus, integrating a rigid adjustable strap. This strap connects to a resilient strap via rigid connectors and anchors at the lower dorsal aspect of the user's standard footwear. These components may overlay a wedge that directs the tension of the resilient straps, maintaining pressure on the lower shin parallel to the surface of the concave TCJ in neutral alignment.

Certain embodiments aim to enhance joint stability and improve range of motion where it is constrained. This constraint could result from joint capsule tightness or muscular dyskinesis caused by the disproportion in size and strength between the larger, more powerful gastrocnemius muscle group and the smaller, weaker Tibialis anterior muscle group. Any restriction from the gastrocnemius can limit TCJ performance, leading to potential ankle sprains, particularly of the lateral ligaments of the ankle. The orthosis may prevent such sprains by promoting proper TCJ roll and glide. It can also function as an ankle retrainer following a healing sprain or post-surgery involving the ankle that required a cast or boot, which could lead to muscle atrophy due to immobilization. The orthosis could also enhance balance by increasing pressure around the ankle, thereby augmenting sensory input.

Depicted in the figures is an ankle orthosis that facilitates proper ankle movement.

Figure 4:
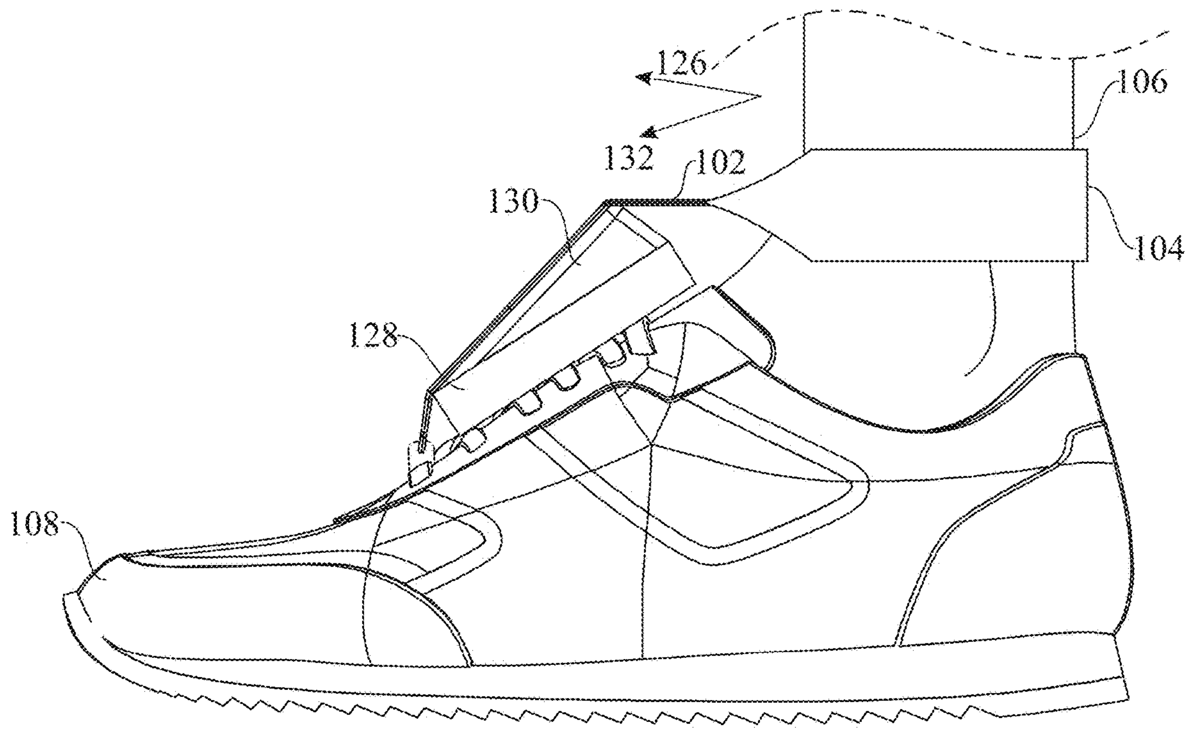
FIG. 4 presents a side view of the ankle orthosis being worn by a user.
Figure 5:
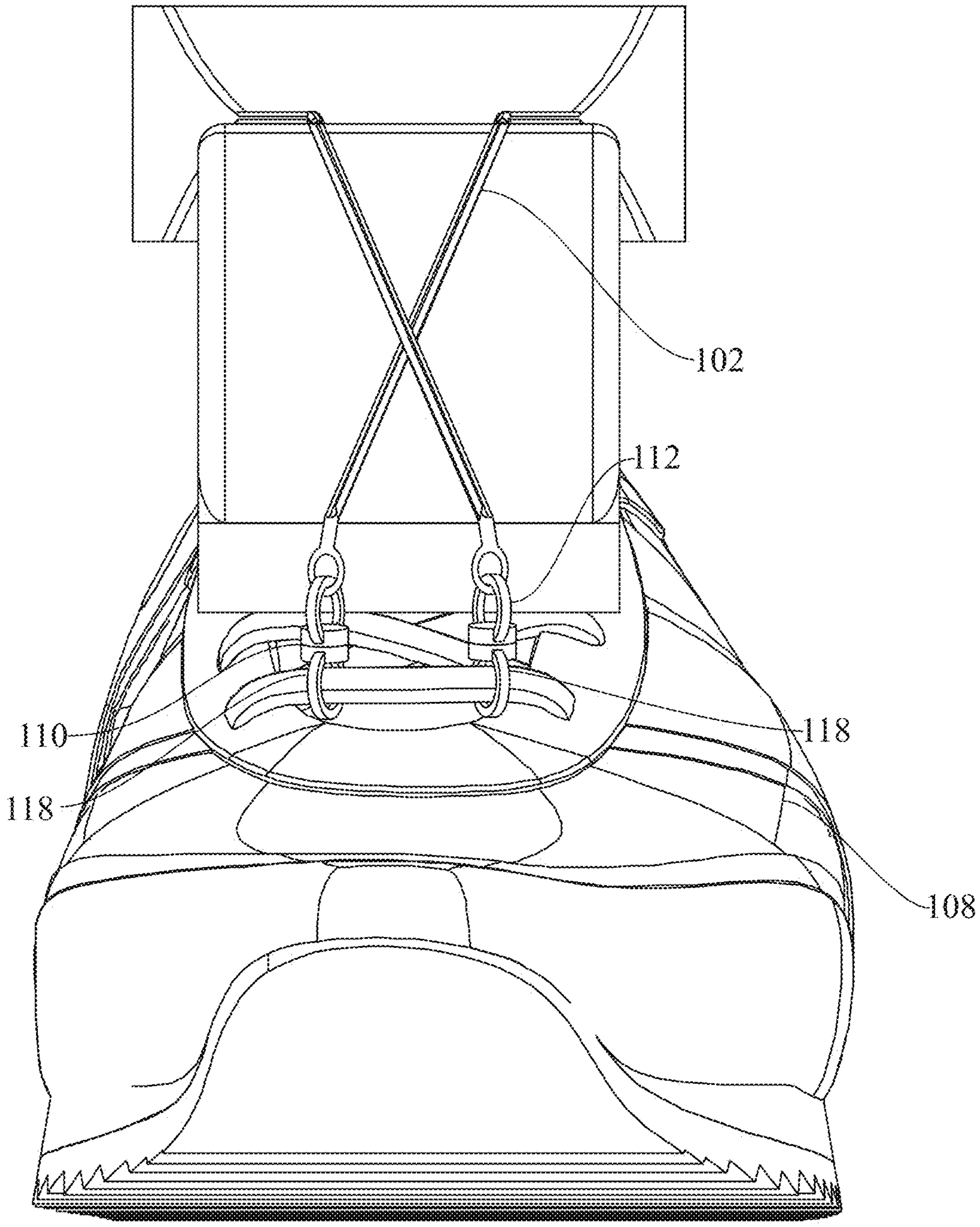
FIG. 5 presents a front view of the ankle orthosis coupled with one or more eyelets of a shoe in accordance with some of the embodiments of the present invention.
Figure 6:
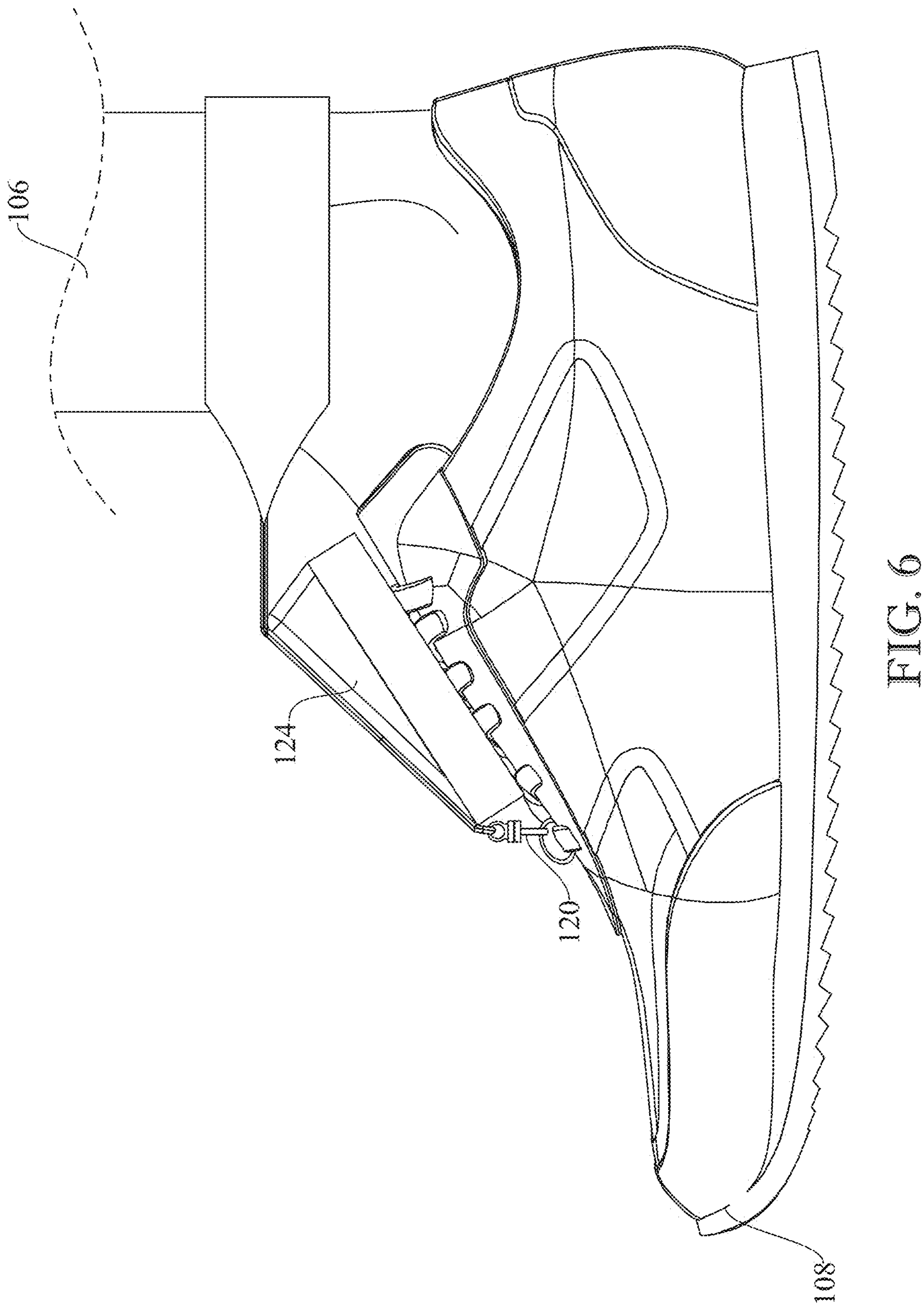
FIG. 6 presents a side view of the ankle orthosis coupled with a shoelace of a shoe in accordance with some of the embodiments of the present invention.
Figure 7:
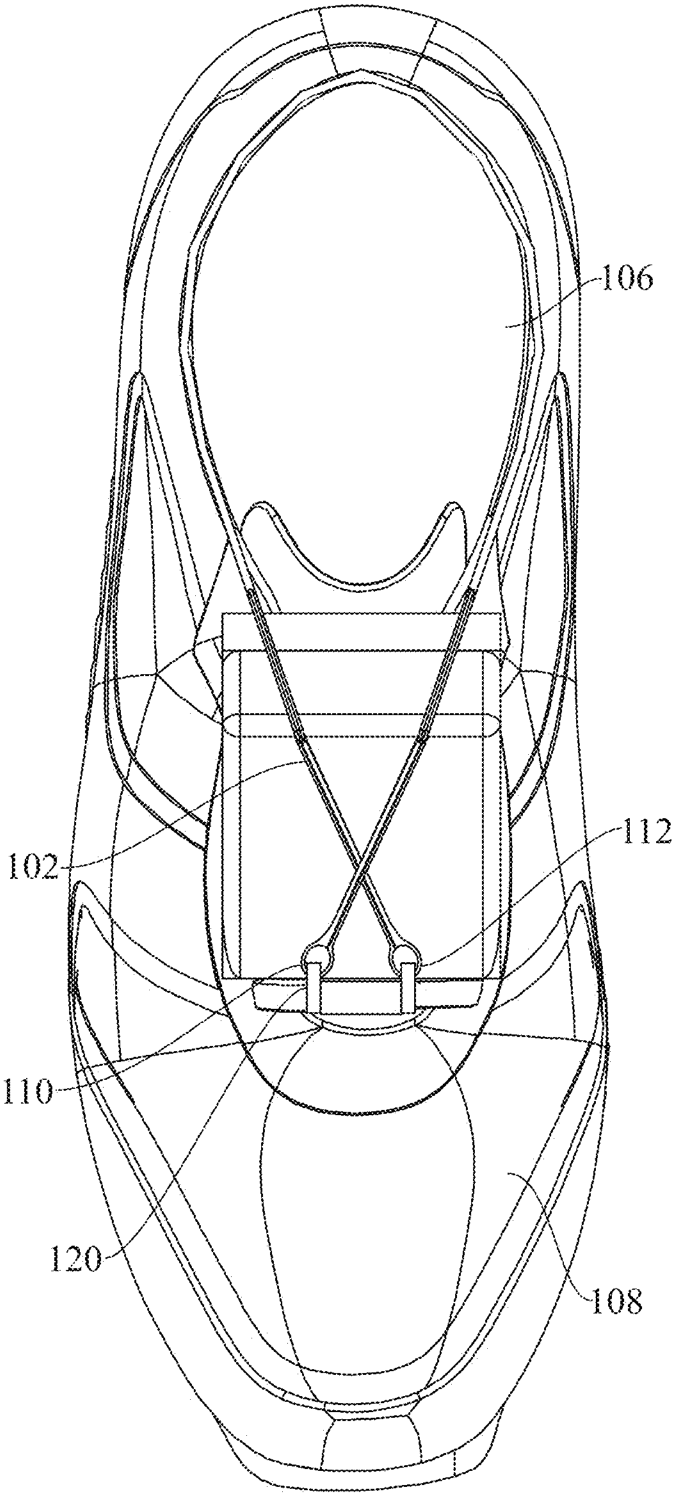
FIG. 7 presents a top view of the ankle orthosis illustrated in FIG. 6.

As shown in FIGS. 1-7, an ankle orthosis 100 is illustrated in accordance with some embodiments. The ankle orthosis 100 includes a strap 102 which, as shown in FIG. 4, extends around the user's leg 106 and may be removably coupled with the user's shoe 108. In certain embodiments, the strap 102 includes a pad 104 located around the user's leg 106. The pad 104 is intended to ensure user comfort and avoid chafing. The strap 102 may include soft material and/or elastic material, and the pad 104 might be composed of soft material, sponge, elastic material, and/or soft leather.

In some embodiments, the strap 102 may include anchors 110 and 112, which may be attached or coupled with the ends 114 and 116 of the strap 102 as shown in FIG. 1. The anchors 110 and 112 might be carabiners, clips, hooks, etc. The strap 102 may be attached or coupled with the shoe 108 using anchors 110 and 112. The anchors 110 and 112 may be directly coupled with one or more eyelets 118 of the shoe 108, with the shoelace 120, or connector 122 attached with the shoelace 120.

Some embodiments feature an ankle orthosis 100 including a support member 124. This support member 124 is situated between the shoe 108 and the strap 102 as shown in FIGS. 1-7. The support member 124 could contain one or more channels (not shown) configured to accommodate the strap 102, keeping it in place during use of the ankle orthosis 100. The support member 124 may be used to keep the strap 102 aligned with the shin bone.

In some embodiments, the support member 124 is adjustable to accommodate different foot sizes or to alter the direction of the forward force. The support member 124 may include a base 128 and a support surface 130. A portion of the support surface 130 may be moved between a first (i.e. raised) position and a second (i.e. lowered) position (not shown).

Figure 8:
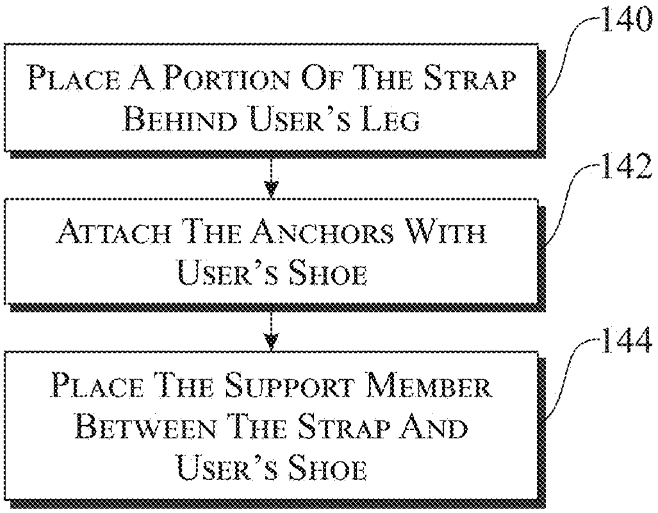
FIG. 8 presents a process in accordance with some embodiments presently disclosed.

FIG. 8 presents a flow diagram depicting the attachment of the ankle orthosis 100. At 140, the user places a portion of the strap 102 behind the user's leg. At 142, the user attaches the anchors 110 and 112 to the user's shoe. At 144, the user places the support member 124 between the strap 102 and user's shoe 108.

It should be understood that the sequence of attachment may vary, and that the support member 124 could be placed above the user's shoe 108 prior to attaching anchors 110 and 112, or after attaching the anchor 110 or 112 with the user's shoe.

In certain alternative embodiments, the ankle orthosis could be equipped with a variety of different types of straps. These straps might not only include a resilient, spring-like nature but could also have adjustable tension settings to provide variable resistance based on the user's needs. This could accommodate differing rehabilitation requirements, allowing a progression from low to high resistance as the user's strength and flexibility improve.

In some embodiments, the strap 102 could be configured to provide additional support structures. For instance, additional padding or an inflatable bladder could be included within or around the strap 102 for enhanced comfort, customizable fit, or additional compression. This could potentially provide increased sensory input, contributing to improved balance performance.

In alternative embodiments, the support member 124 might be made of different materials, such as lightweight metal, hard plastic, or composite material, to offer both rigidity and lightweight characteristics. It could also be crafted to include more channels to accommodate multiple straps, potentially providing additional control and stabilization.

The anchors 110 and 112, in some embodiments, might also include quick-release mechanisms for easy attachment and detachment from the shoe. They could be designed to accommodate various types of footwear, expanding the usability of the orthosis beyond conventional shoes to boots, athletic shoes, or even certain types of specialized footwear such as cleats or ballet shoes.

In some alternative embodiments, the ankle orthosis might incorporate smart technologies, such as sensors to monitor range of motion, pressure, or balance. These could provide real-time feedback to users or healthcare providers, facilitating monitoring of progress and adjustment of treatment plans as necessary.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. An ankle orthosis comprising:

a conforming back strap configured to attach to a wearer's distal above the lateral and medial malleolus;

a rigid adjustable strap coupled to the back strap;

a resilient strap connected to the rigid adjustable strap, the resilient strap being configured to elastically stretch in response to movement and to exert a restoring tensile force when elongated;

one or more anchors coupled to a distal end of the resilient strap and configured to secure the orthosis to a wearer's footwear; and a wedge configured to be positioned between the rigid adjustable strap and the shin of the wearer, the wedge being oriented to direct force from the resilient strap along a vector generally parallel to a surface of the talocrural joint when the ankle is in a neutral position;

wherein the orthosis is configured to facilitate posterior talar glide and controlled dorsiflexion, and to enhance ankle joint mobility by promoting arthrokinematic and osteokinematic motion patterns.

2. The ankle orthosis of claim 1, wherein the resistive strap is akin to a spring.

3. The ankle orthosis of claim 1, wherein the back strap, adjustable strap, resistive strap and anchors are overlaid by a customizable spandex cover.

4. The ankle orthosis of claim 1, further comprising a support member that is adjustable to accommodate different size feet.

5. The ankle orthosis of claim 4, wherein the support member is adjustable to change the direction of the forward force exerted by the resilient strap.

6. The ankle orthosis of claim 1, wherein the orthosis promotes proper ankle roll and glide in accordance with fundamental arthrokinematics and osteokinematics.

7. The ankle orthosis of claim 1, wherein the orthosis encourages appropriate Talocrural joint function.

8. The ankle orthosis of claim 1, wherein the orthosis assists transition from plantarflexion to dorsiflexion.

9. The ankle orthosis of claim 1, wherein the orthosis supports dynamic movement.

10. The ankle orthosis of claim 1, wherein the orthosis promotes balance via increased sensory input from distal shin compression.

11. The ankle orthosis of claim 1, wherein the orthosis decreases potential for ankle sprains.

12. The ankle orthosis of claim 1, wherein the orthosis aids in retraining and recovery of the ankle following trauma.

13. The ankle orthosis of claim 1, wherein the orthosis aids in recovery of the ankle following surgery.

14. The ankle orthosis of claim 1, wherein the orthosis aids in recovery of the ankle following overuse.

15. The ankle orthosis of claim 1, wherein the orthosis is designed to secure to a wearer's conventional shoe at the distal dorsal aspect.

16. The ankle orthosis of claim 1, wherein rigid connectors affix the resilient strap to the adjustable strap.

17. The ankle orthosis of claim 1, wherein the back strap is configured to provide comfort to the user and prevent chafing.

18. An ankle orthosis comprising:

a conforming back strap configured to attach to a wearer's distal shin above the lateral and medial malleolus;

a rigid adjustable strap coupled to the back strap;

a resilient strap connected to the rigid adjustable strap, the resilient strap being configured to elastically stretch in response to movement and to exert a restoring tensile force when elongated;

one or more anchors coupled to a distal end of the resilient strap and configured to secure the orthosis to a wearer's footwear; and a wedge configured to be positioned between the rigid adjustable strap and the shin of the wearer, the wedge being oriented to direct force from the resilient strap along a vector generally parallel to a surface of the talocrural joint when the ankle is in a neutral position;

wherein the orthosis is configured to facilitate posterior talar glide and controlled dorsiflexion, and to enhance ankle joint mobility by promoting arthrokinematic and osteokinematic motion patterns.

19. An ankle orthosis comprising:

a conforming back strap configured to attach to a wearer's distal shin above the lateral and medial malleolus;

a rigid adjustable strap coupled to the back strap;

a resilient strap connected to the rigid adjustable strap, the resilient strap being configured to elastically stretch in response to movement and to exert a restoring tensile force when elongated;

one or more anchors coupled to a distal end of the resilient strap and configured to secure the orthosis to a wearer's footwear;

a wedge configured to be positioned between the rigid adjustable strap and the shin of the wearer, the wedge being oriented to direct force from the resilient strap along a vector generally parallel to a surface of the talocrural joint when the ankle is in a neutral position; and a support member that is adjustable to accommodate different size feet, wherein the support member is adjustable to change the direction of the forward force exerted by the strap;

wherein the orthosis is configured to facilitate posterior talar glide and controlled dorsiflexion, and to enhance ankle joint mobility by promoting arthrokinematic and osteokinematic motion patterns.

* * * * *